(12) United States Patent
Watanabe et al.

(10) Patent No.: US 6,752,838 B2
(45) Date of Patent: Jun. 22, 2004

(54) FABRIC PROTECTANT AGAINST PESTS

(75) Inventors: Keisuke Watanabe, Ashiya (JP); Masayo Sugano, Osaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/964,767

(22) Filed: Sep. 28, 2001

(65) Prior Publication Data
US 2002/0058074 A1 May 16, 2002

Related U.S. Application Data

(62) Division of application No. 09/252,240, filed on Feb. 18, 1999, now Pat. No. 6,436,150.

(30) Foreign Application Priority Data

Feb. 18, 1998 (JP) .......................................... 10-035782

(51) Int. Cl.⁷ ......................... A01N 65/00; D06M 13/00
(52) U.S. Cl. ....................... 8/115.6; 424/403; 424/725; 424/733; 424/739; 424/745; 424/756; 424/778
(58) Field of Search ........................... 8/115.6; 424/403, 424/725, 733, 739, 745, 756, 778, 755

(56) References Cited

U.S. PATENT DOCUMENTS

| | | | | |
|---|---|---|---|---|
| 5,679,351 A | * | 10/1997 | Walter et al. | 424/725 |
| 5,688,509 A | * | 11/1997 | Radwan et al. | 424/405 |
| 5,839,224 A | | 11/1998 | Emerson et al. | |
| 6,231,865 B1 | * | 5/2001 | Hsu et al. | 424/739 |

FOREIGN PATENT DOCUMENTS

DE 3901341 A1 7/1990

OTHER PUBLICATIONS

Takayoshi, "Nontoxic Insect Repellent Compositions for Protecting Clothes From Damage by Moth and Other Insects", Publ. No. JP 5097618 A, JP 91–285670 Ken Sakurabayashi, Declaration, May 28, 2001.

Linsig et al., "Synergistic Mixture of Essential Oils or Essences—Useful in Pharmaceutical, Veterinary, Plant Treatment, . . . and Deodorant", Derwent–ACC–No: 1998–207871, Derwent–Week: 199819.

"Control Agent for Insect Pests for Fabric—Comprising Essential Oil from Juniperus, Cymbopogon . . . and/or Chamaecyparis spp.", Derwent ACC–No. 1993–164313, Abstract Publ. No. JP05097618A.

Seiyaku et al., "Nontoxic Insect Repellant Compositions for Protecting Clothes from Damage by Month and Other Insects", Chemical Abstracts, JP 05 097618, vol. 119, No. 9, Aug. 30, 1993, Abstract No. 88945.

The Basic Archives, "Sensory and Chemical Evaluation of Tropical Grass Oils", [POM—97011], (1997).

AromaWeb, E.O. Profiles, Palmarosa (Rose Geranium), (1997–00).

Plarre et al., "Effects of Oil of Cloves and Citronello, Two Commerically Available Repellents, . . . Tineola bisselliella Hum", Database Cropu, XP002101876, Abstract, & Anz. Schadelingskd. Planz. Umweltschutz, vol. 70, No. 3, 1997, pp. 45–50.

* cited by examiner

*Primary Examiner*—Herbert J. Lilling
(74) *Attorney, Agent, or Firm*—Fitch, Even, Tabin & Flannery

(57) ABSTRACT

A fabric protectant comprising of a carrier and a plant oil selected from the group consisting of horseradish oil, bay oil, basil oil, calamus oil, ginger oil, palmarosa oil, cinnamon oil, ylang—ylang oil, perilla oil, valerian oil, clove oil, star anise oil, milfoil oil, fennel oil, oregano oil and angelica oil, efficaciously controls fabric-related pests. In addition, a method of protecting fabric which comprises dispersing, spraying, spreading and setting an effective amount of the plant oil selected from the group given above is an excellent method to control fabric-related pests.

5 Claims, No Drawings

FABRIC PROTECTANT AGAINST PESTS

This is a divisional application of co-pending U.S. application Ser. No. 09/252,240, filed on Feb. 18, 1999 now U.S. Pat. No. 6,436,150.

FIELD OF THE INVENTION

The present invention relates to a fabric protectant that has a plant oil as an active ingredient.

BACKGROUND OF THE INVENTION

A fabric protectant is usually deployed to keep treated fabric unencumbered from certain damages. One of the damages a fabric material may encounter is related to pests. An assortment of pests are known to damage fabrics by means such as feeding upon the fabric material. Clothing may be victim to these fabric-related pests and a fabric protectant against the said fabric-related pests would be an advantage.

SUMMARY OF THE INVENTION

The objective of the present invention is to serve a fabric protectant that efficaciously controls fabric-related pests. The plant oils of horseradish oil, bay oil, basil oil, calamus oil, ginger oil, palmarosa oil, cinnamon oil, ylang—ylang oil, perilla oil, valerian oil, clove bud oil, star anise oil, milfoil oil and fennel oil surprisingly control fabric-related pests efficaciously and, therefore, are utilized to produce the fabric protectant of the present invention.

DETAILED DESCRIPTION OF THE INVENTION

The fabric protectant of the present invention comprises a specific plant oil. The plant oil utilized in the present invention (hereinafter, the present oil), which is selected from the group consisting of horseradish oil, bay oil, basil oil, calamus oil, ginger oil, palmarosa oil, cinnamon oil, ylang—ylang oil, perilla oil, valerian oil, clove bud oil, star anise oil, milfoil oil and fennel oil, oregeno oil and angelica oil. The plant oils utilized in the present invention are standardly essential oils. Therefore, horseradish oil can be obtained by steam distillation of horseradish (*Cochlearia armoracia*), bay oil can be obtained by steam distillation of bay (*Pimenta racemosa*) leaves, basil oil can be obtained by steam distillation of basils (Ocimum spp.), calamus oil is can be obtained by steam distillation of sweet flag (*Acorus calamus*) rhizomes, ginger oil can be obtained by steam distillation of ginger (*Zingiber officinale*), palmarosa oil can be obtained by steam distillation of rosha grass (*Cymbopogon martinii*), cinnamon oil can be obtained by steam distillation of cassia or cinnamon (Cinnamomum spp.) trees, scrubs, barks or leaves, ylang—ylang oil can be obtained by steam distillation of ylang—ylang (*Cananga odorata*) flowers, perilla oil can be obtained by steam distillation of Perilla spp leaves, flowers or seeds, valerian oil can be obtained by steam distillation of garden heliotrope (*Valeriana officinalis*) rhizomes, clove oil can be obtained by steam distillation of clove (*Eugenia caryophyllata*) buds, stems or leaves, star anise oil can be obtained by steam distillation of star anise (*Illicium verum*) fruits or leaves, milfoil oil can be obtained by steam distillation of milfoil (*Achillea millefolium*), fennel oil can be obtained by steam distillation of wild marjoram (*Origanum vulgare*) and angelica oil can be obtained by steam distillation of Angelica spp. Each present oil may be extracted from the botanical source according to the methods disclosed in *Kouryou Kagaku Souran* (Okuda; Hirokawa shoten publication, 1967). It is also possible to purchase plant oils from the market.

The fabric protectant sets forth efficacious activity against fabric-related pests which mainly damage fabrics. Examples or fabric related pests include Tinea such as case-bearing clothes moth (tinea translucens) and casemaking clothes moth (*Tinea pellionella*), Tineola such as common clothes moth and webbing clothes moth (*Tineola bisselliella*), Attagenus such as black carpet beetle (Attagenus unicolor japonicus) and *Attagenus unicolor*, Anthrenus such as varied carpe beetle (*Anthrenus verbasci*), Hofmannophila such as brown house mouth (*Hofmannophilia pseudospretella*), Endrosis such as white-shouldered house moth (*Endrosis sarcitrella*), and Dermestes such as hide beetle (*Dermestes maculatus*), larder beetle (*Dermestes lardarius*), *Dermestes haemorrhoidalis* and *Dermestes perunvinus*.

Formulations of the fabric protectant may comprise of carriers, in addition to the present oils, but a formulation solely comprising one or more of the present oils is also effective. Cream formulations and liquid formulations such as an aerosol, are examples of formulations that comprise a carrier. A formulation comprising resins usually comprises synthetic resins that were previously impregnated with any present oil. Furthermore, a gel formulation and formulation comprising of paper or bisques wherein the paper or bisque is previously impregnated with any present oil, are also possible formulations of the fabric protectant. Dissolving the plant oil or oils in a appropriate solvent, such as acetone, is a suitable means to impregnate the paper in formulating the formulation comprising an impregnated paper. The fabric protectant usually utilizes formulations comprising the carrier.

Suitable carriers for the liquid formulation include water; alcohols such as methanol, ethanol, glycerin and polyethylene glycol; ethers such as tetrahydrofuran and dioxane; aliphatic hydrocarbons such as hexane, kerosene, paraffin and petroleum benzine; or esters such as ethyl acetate.

Suitable carriers for the cream formulation include hydrocarbons such as liquid paraffin, vaseline and solid paraffin; silicones such as dimethylsiloxane, colloidal silica and bentonite; alcohols such as ethanol, stearyl alcohol, lauric alcohol, polyethylene glycol, glycerin; carboxylic acids such as lauric acid and stearic acid; bees wax; and esters such as lanolin.

The formulations comprising a carrier, such as the liquid formulation and cream formulation, may also additionally comprise auxiliary agents such as emulsifiers, spreading/wetting agents, suspensible agents, preservatives and propellants, or coating agents. More specifically, examples of emulsifiers include soaps, polyoxyethylene fatty acid alcohol ethers such as polyoxyethylene oleyl ether, polyoxyethylenealkyl aryl ethers such as polyoxyethylenenonyl phenyl ether, polyoxyethylene fatty acid esters, fatty acid glycerides, sorbitan fatty acid esters, higher alcohols sulfates and alkylarylsulfonic acid salts such as sodium dodecylbenzenesulfonate;

spreading/wetting agents include glycerin and polyethylene glycol;

suspensible agents include casein, gelatin, alginic acid, carboxymethylcellulose, gum arabic, hydroxypropylcellulose and bentonite;

perservatives include methyl p-hydroxybenzoate, ethyl p-hydroxybenzoate, isopropyl p-hydroxybenzoate and butyl p-hydroxybenzoate;

propellents include dimethyl ether, chlorofluorocarbons and carbon dioxide;

and coating agents include nitrocellulose, acetylcellulose, acetylbutylcellulose, methylcellulose derivatives, polyvinyl alcohols and vinyl resins such as vinyl acetate resins.

Examples of synthetic resins for the formulation comprising resins (hereinafter, resin formulation) include polyethylene; polypropylene; a copolymer composition of ethylene and a monomer that comprises a polar group, such as an ethylene-vinylacetate copolymer, ethylene-methyl(meta) acrylate copolymer, ethylene-ethylacrylate copolymer and ethylene-vinylacetate-methyl(meta)acrylate copolymer; and synthetic resins comprising chlorine atom(s), such as polyvinylchloride and polyvinylidenechloride. The ethylene-vinylacetate copolymer and ethylene-methyl(meta)acrylate copolymer are the preferable synthetic resins, because ethylene-vinylacetate copolymer and ethylene-methyl (meta)acrylate exceed in moldability under a relatively low heat condition, as well as the ability to retain, diffuse, and stabilize the plant oils.

The synthetic resins may comprise the plant oils by means of impregnating the essential oil to the said resin. Methods of impregnation include, the present oil itself impregnating the synthetic resin, dissolving the present oil in an appropriate solution such as acetone and then impregnating the synthetic resin with the obtained solution, or a method wherein a concentrated master pellet is formed.

In the master pellet method, one or more of the present oils in the liquid state is incorporated to the synthetic resins, and then mixed. The mixed solution may be diluted to the appropriate concentration, if necessary, with additions of synthetic resin and formed to the objective mold such as a film, sheet and net. Methods of forming the obtained synthetic resins include the injection molding method utilized by heat-treated resins, inflation molding or spinning.

The amount of the present oils within the formulations mentioned earlier differs upon the use and formulation variation, but the liquid or cream formulations may comprise the present oils from 0.1 to 50% by weight, preferably from 1 to 20% by weight. It is standard for the resin formulation to comprise the present oils from 1 to 40% by weight, and preferably from 5 to 30% by weight. The pest repelling activity will not be efficient if the resin formulation lacks the present oils by 1% by weight. An unfavorable tacky sensation, such as adhesion, procures when the resin formulation comprises the present oils at more than 40% by weight because of the tendency for the present oils to bleed at the surface of the molding.

The present protectant may further comprise of other pesticides, pest repellents, synergists, anti-oxidants and UV-absorption agents, as well as other additional agents such as fragrances, dyes and pigments.

Examples of the pesticides include empenthrin (1-ethynyl-2-methyl-2-pentenyl-d-cis, trans-chrysanthemate (cis:trans ratio=2:8)), 1-ethynyl-2-fluoro-2-pentenyl d-trans-3-(2,2-dichlorovinyl)-2,2-dimethylcyclopropanecarboxylate and transfluthrin. Examples of the pest repellents include caran-3,4-diol, DEET, p-menthane-3,8-diol, 2, 3, 4, 5-bis ($\Delta^2$-butylene)tetrahydrofurfural, di-n-propylisocicholonate, di-n-butyl succinate, 2-hydroxyoctylsulfide and (N-carbo-sec-butyloxy)-2-(2'-hydroxyethyl piperidine). An example of the surfactants is N-(2-ethylhexyl)-8,9,10-trinorborn-5-ene-2,3-dicarboxyimide (MGK-264). Examples of the anti-oxidants include butylhydroxyanisole, dibutylhydroxytoluene, tocopherol, and γ-orizanole.

The fabric protectant may be utilized by dispersing, spraying, spreading or setting within any appropriate area wherein pest controlling activity is deemed necessary. Dressers, drawers, cases and closets are areas wherein a fabric-related pest may invade. Furthermore, the fabric protectant may also be utilized by wrapping clothing around the fabric protectant such as paper or resin moldings that comprise the present oils.

EXAMPLES

Hereinafter, the formulation and test examples further explain the present invention, but does not limited the present invention in anyway. Hereinafter, parts represents parts by weight.

Formulation Example 1

Each present oil was formulated into an aerosol by the following procedure.

Ten (10) parts of a present oil are dissolved in ethanol to make the complete body 35 parts, and are packed into an aerosol device. After a valve is attached to the each aerosol device, 65 parts of a 1:1 mixture comprising of fron 11 and 12 is charged through the valve portion under pressure to acquire an aerosol.

Formulation Example 2

Ten (10) parts of stearic acid, 2 parts of cetyl alcohol, 1 part of laonoline, 2 parts of liquid paraffin and 62 parts of water are added to 10 parts of horseradish oil. After the said mixture is heated, melted and mixed, 13 parts of glycerin are further incorporated and well mixed to acquire a cream formulation Formulation Example 3

Each present oil was formulated into a pellet and subsequently molded to a 1 mm thick sheet, by the following procedure.

Thirty (30) parts of a present oil and 70 parts of ethylene-methylmetacrylate copolymer (Sumitomo Chemical Company, Acrylift WH202) are stirred by using a closed pressurized kneader for 15 minutes and then formed into a master pellet. A hundred (100) parts of the master pellet and 200 parts of the matrix resin of ethylene-methylmetacrylate copolymer are stirred in a closed pressurized kneader for 15 minutes, fed into an extruder and have hot cuts performed while being extruded. A pellet comprising 10% by weight of a present oil is obtained. A said pellet was then molded with a T die extrusion machine to acquire a 1 mm thick sheet.

Formulation Example 4

Each present oil is formulated into a formulation comprising an impregnated paper, by the following method.

A thousand micrograms (100 μg) of a present oil is dissolved in an appropriate amount of acetone, uniformly spread on a 2 cm×2 cm filter paper with a thickness of 0.3 mm and then dried with acetone. A formulation comprising an impregnated paper is acquired.

The effectiveness of the present oils as an active ingredient is set forth in the test examples. All the horseradish oil utilized in the test examples are available from the market (Takasago International Corporation)

Test Example 1

Each present oil was tested by the following procedure.

One-tenth milliliter (0.1 ml) of an acetone solution comprising 1% by weight of a present oil is impregnated to 1 cm×1 cm muslin wool fabric and the impregnated wool fabric is placed on the bottom area of a plastic cup with a volume of 60 cm³. Subsequently, a cover comprising of a 1.5 cm diameter hole was placed on the said cup. The said cup was then placed on the floor within a 20 cm×20 cm×28.5 cm nylon gauze cage. The cage was infested with an appropriate amount of adult webbing clothes moths, and was preserved at 25° C. and 60% humidity. Twenty-four hours. (24 hrs.) later, the number of living and dead pests within the cup were surveyed. The number of eggs on the muslin wool were also surveyed by utilizing a microscope. The test was repeated.

The test was further carried out for a control. As the control, a muslin wool fabric free from plant oil treatment and the same procedure was utilized.

The results are given in the following table.

TABLE 1

| utilized present oil | total # of moths used in the test | observation of cup | | |
|---|---|---|---|---|
| | | # of dead moths | # of surviving moths | # of eggs |
| 1. Horseradish oil | 80 | 28 | 5 | 12 |
| control | 80 | 0 | 14 | 79 |
| 2. Bay oil | 100 | 29 | 3 | 1 |
| control | 100 | 0 | 27 | 63 |
| 3. Basil oil | 100 | 13 | 12 | 27 |
| control | 100 | 0 | 30 | 127 |
| 4. Calamus oil | 100 | 1 | 18 | 3 |
| control | 100 | 0 | 21 | 104 |
| 5. Ginger oil | 100 | 8 | 11 | 3 |
| control | 100 | 0 | 30 | 226 |
| 6. Palmarosa oil | 100 | 26 | 1 | 1 |
| control | 100 | 0 | 33 | 195 |
| 7. Cinnamon oil | 100 | 16 | 5 | 9 |
| control | 100 | 1 | 27 | 247 |
| 8. Ylang-ylang oil | 100 | 0 | 9 | 30 |
| control | 100 | 0 | 34 | 235 |
| 9. Perilla oil | 100 | 4 | 10 | 1 |
| control | 100 | 0 | 18 | 96 |
| 10. Valerian oil | 100 | 9 | 9 | 13 |
| control | 100 | 0 | 25 | 124 |
| 11. Clove oil | 100 | 22 | 0 | 1 |
| control | 100 | 1 | 32 | 244 |
| 12. Star anise oil | 100 | 5 | 5 | 11 |
| control | 100 | 0 | 26 | 182 |
| 13. Milfoil oil | 100 | 10 | 10 | 22 |
| control | 100 | 0 | 14 | 106 |
| 14. Fennel oil | 100 | 16 | 7 | 16 |
| control | 100 | 0 | 21 | 111 |
| 15. Oregano oil | 100 | 22 | 2 | 1 |
| control | 100 | 0 | 21 | 85 |
| 16. Angelica oil | 100 | 3 | 16 | 8 |
| control | 100 | 0 | 32 | 61 |

Test Example 2

A 2 cm×2 cm muslin wool fabric was impregnated dropwise with 0.1 mL of an acetone solution comprising 1% by weight of horseradish oil and was placed on the bottom of a 50 cm³ polyethylene cup. The said cup was then infested with 10 middle instar larvae, and was preserved for 3 days at 25° C. and 60% humidity. The surviving and moribund test insects on or off the fabric were observed 3 days later, as well as the degree of muslin wool fabric damaged.

The fed amount were given the following grades,

++++: high degree of fabric damaged

+++: an average degree of the fabric damaged

++: a low degree of the fabric damaged

+: a lower degree of fabric damaged

−: no observable amount of fabric damaged

Furthermore, a control was performed with the use of a muslin wool fabric that is deficient of plant oil treatment.

As a result, the area treated with horseradish oil had all the test insects dead and off of the fabric and with a − grade for the degree of wool consumed. The non-treated area had all the test insects surviving and on the fabric and had a ++++ grade of wool consumed.

We claim:

1. A method of protecting fabric against pests which comprises dispersing, spraying, spreading or setting an effective amount of bay oil on the fabric or to a place where pests invade and where the fabric is located.

2. A method of protecting fabric against pests which comprises dispersing, spraying, spreading or setting an effective amount of palmarosa oil on the fabric or to a place where nests invade and where the fabric is located.

3. A method of protecting fabric against pests comprising applying a solution containing an effective amount of a plant oil which includes at least one member selected from the group consisting of bay oil, basil oil and palmarosa oil to said fabric, whereby said fabric is protected against said pests, from said pests laying eggs in or on said fabric, and against larvae hatching from eggs that may have been laid, wherein said fabric comprises muslin wool.

4. The method according to claim 3, wherein said solution contains up to 50% by weight of said plant oil.

5. The method according to claim 3, wherein said solution contains up to 20% by weight of said plant oil.

* * * * *